United States Patent [19]

Hope

[11] Plant 4,806

[45] Jan. 19, 1982

[54] KALANCHOE NAMED WARRIOR

[75] Inventor: Claude Hope, Cartago, Costa Rica

[73] Assignee: Pan-American Plant Company, West Chicago, Ill.

[21] Appl. No.: 150,592

[22] Filed: May 16, 1980

[51] Int. Cl.[3] ..... A01H 5/00
[52] U.S. Cl. ..... Plt./68
[58] Field of Search ..... Plt./68

*Primary Examiner*—Robert E. Bagwill

*Attorney, Agent, or Firm*—Rummler and Snow

[57] ABSTRACT

A new and distinct variety of kalanchoe particularly suitable for year-around four or six inch pot plant production and distinguished by its dark red flowers held high above an abundant display of large, shiny, dark green leaves. This plant has a ten to twelve week response, a strong, vigorous and upright growth habit, and a profuse production of blooms borne on strong, rigid stems.

2 Drawing Figures

BACKGROUND OF THE NEW PLANT

This kalanchoe cultivar originated as a seedling of unknown parentage discovered by me at breeding facilities in Cartago, Costa Rica, where I have been breeding and growing kalanchoe plants with the object of developing a new and superior red variety. The distinctive character of this plant, compared with other red varieties such as "Conquistador" (U.S. Plant Pat. No. 4,568), and "Toltec" (U.S. Plant Pat. No. 4,342), led me to propagate this plant by cuttings and further propagation in that manner through several successive generations at Cartago, Costa Rica, has shown that its novel characteristics hold true from generation to generation and appear to be firmly fixed. Although its genealogy has been lost, the origin of this new plant is identified in my records as Seedling No. K-78-92-R and production on a commercial scale is now being done by means of vegetative cuttings at West Chicago, Ill., and at Parrish, Fla.

DESCRIPTION OF THE DRAWINGS

My new kalanchoe plant is illustrated by the accompanying photographic drawings, of which sheet 1 shows the growth and flower display characteristics of the new plant and sheet 2 is a close-up view of the flowers, the drawing having been hand-painted to show the true colors of the flowers according to the following specification.

DESCRIPTION OF THE NEW PLANT

The following is a detailed description of this new kalanchoe cultivar based upon observations of the new plant grown in greenhouse at West Chicago, Ill., the color designations being according to The R.H.S. Colour Chart published by The Royal Horticultural Society of London, England.

THE PLANT

Origin: Seedling.
Parentage: Unidentified.
Classification:
- *Botanic.*—*Kalanchoe blossfeldiana.*
- *Commercial.*—Kalanchoe pot plant.

Form: Upright vase-shaped bush.
Height: Variable according to age and culture.
Growth: Vigorous, strong and with rapid growth rate.
Branching character: Caespitose.

Foliage:
- *Quantity.*—Abundant.
- *Size of leaf.*—About 30 to 70 mm. long and about 20 to 50 mm. wide.
- *Shape.*—Ovate with cuneate base and repand margins.
- *Surface aspect.*—Smooth and glossy.
- *Ribs and veins.*—Netted.
- *Color.*—Upper side — 137A. Under side — 137C.
- *Petioles.*—Length — about 5 to 12 mm.

THE BUD

Size: Variable.
Shape: Long and pointed.
Opening rate: Normal.
Petal color: When sepals first divide — Pink. When petals begin to unfurl — 43C.
Sepals: Four in number, awl shaped and hooded over the bud. The sepals are upstanding when the flower opens.
- *Color.*—Inside surface — 138D. Outside surface — 138D.

Calyx:
- *Shape.*—Pear-shaped.
- *Size.*—Small.
- *Splitting.*—The calyx splits.
- *Aspect.*—Smooth.

THE FLOWER

Blooming habit: Intermittent.
Recommended flowering: Year around with photoperiod control.
Response: 10 to 12 weeks.
Blooms: Borne in a panicle.
- *Size.*—Small. Diameter: 5 to 10 mm. Depth: approximately 10 mm.
- *Shape.*—Cup-shaped when bloom first opens, becoming funnel form as the bloom matures.

Petalage:
- *Number of petals.*—Four, rounded, somewhat spoon-shaped with entire margin and rounded apex.
- *Texture.*—Soft.
- *Appearance.*—Satiny.
- *Color.*—As observed in Fall season at West Chicago, Ill.: upper surface — 44A–45B, depending upon season and temperature. Reverse side — 44D.

Peduncle:

*Length.*—Variable.

*Strength.*—Rigid and erect.

*Color.*—137D.

Discoloration after full bloom: Very little.

Effect of wet or hot weather: Very little.

Persistence: Flowers hang on and dry.

Fragrance: None.

Lasting quality: On plant — 4 to 6 weeks.

REPRODUCTIVE ORGANS

Stamens: Number — 8.

*Arrangement.*—Didynamous.

*Anthers.*—Size: insignificant. Color: yellow.

*Filaments.*—Length: insignificant. Color: yellow.

*Pollen color.*—Yellow.

Pistils:

*Number.*—4.

*Styles.*—Length: insignificant. Color: green.

*Stigmas.*—Color: green changing to white.

Ovaries: Four superior.

This new kalanchoe variety most nearly resembles the varieties "Conquistador" (U.S. Plant Pat. No. 4,568) and "Toltec" (U.S. Plant Pat. No. 4,342) except that its flowers are a darker red than either of the said varieties and there is no fasciation as there is in "Toltec". This kalanchoe cultivar blooms profusely with masses of flowers held on sturdy, rigid stems high above and between the dark green leaves thereby presenting a spectacular display in a pot plant of average height.

I claim:

1. A new and distinctive kalanchoe cultivar, substantially as herein shown and described, characterized by its massed panicels of small flowers of dark red color, its strong, vigorous growth habit, profuse production of flowers, and its year-around flowering ability under photoperiod control.

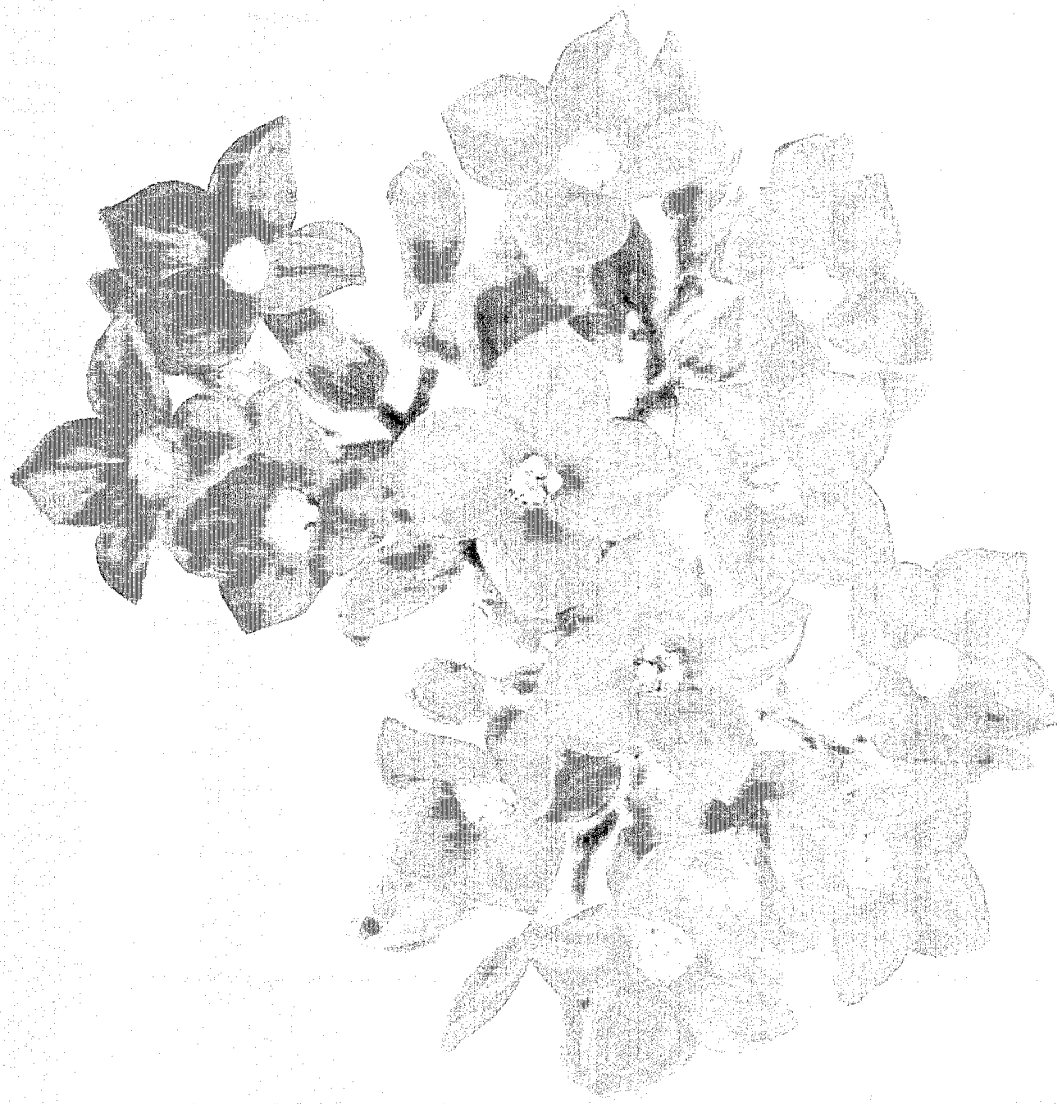

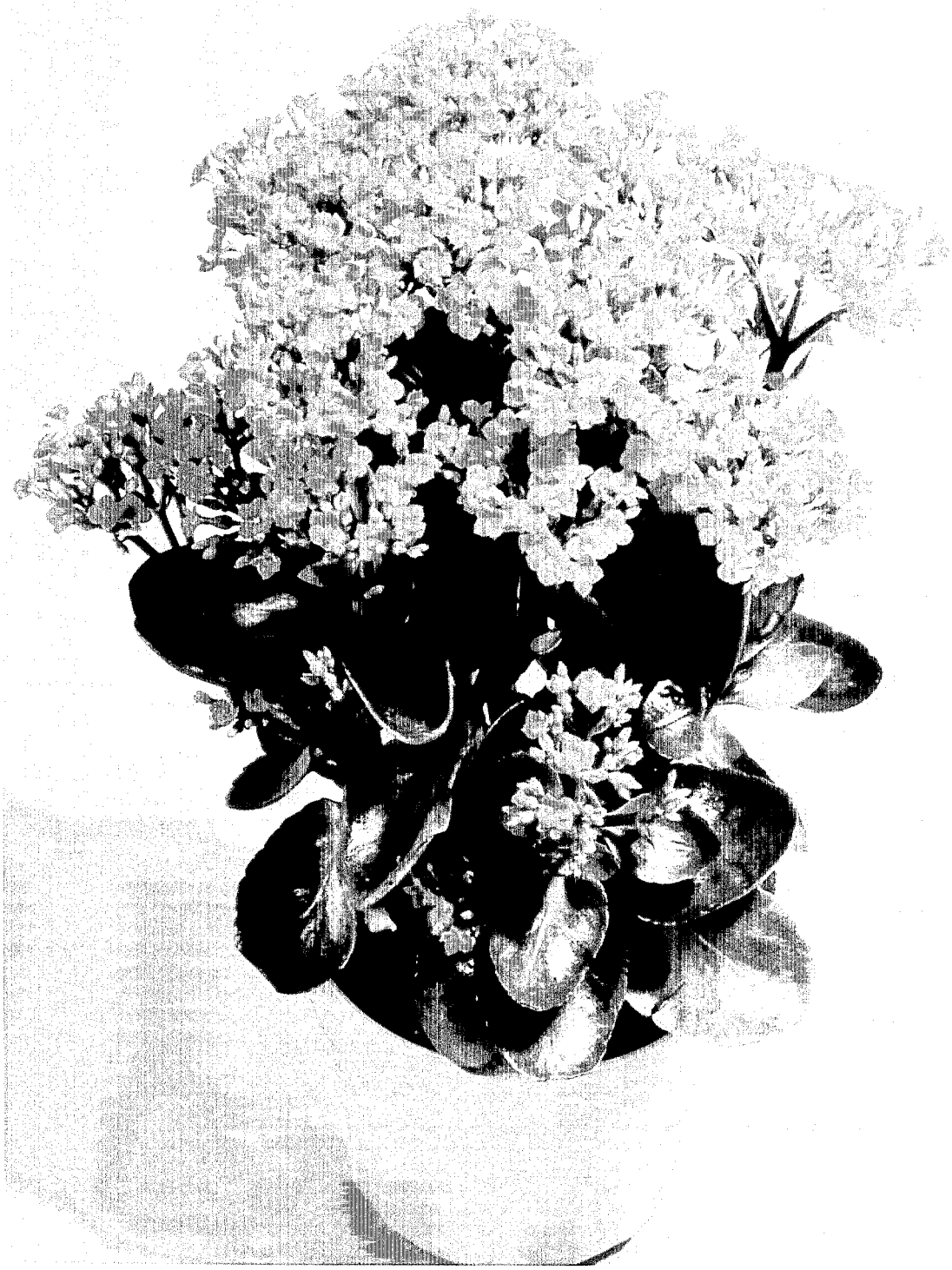

* * * * *